United States Patent
Courtney, Jr. et al.

(10) Patent No.: US 11,278,428 B2
(45) Date of Patent: Mar. 22, 2022

(54) OSTEOTOME EXTRACTOR

(71) Applicant: Howmedica Osteonics Corp., Mahwah, NJ (US)

(72) Inventors: Robert Courtney, Jr., Pierceton, IN (US); Jeffrey M. Ondrla, Warsaw, IN (US)

(73) Assignee: HOWMEDICA OSTEONICS CORP., Mahwah, NJ (US)

( * ) Notice: Subject to any disclaimer, the term of this patent is extended or adjusted under 35 U.S.C. 154(b) by 303 days.

(21) Appl. No.: 16/249,720

(22) Filed: Jan. 16, 2019

(65) Prior Publication Data

US 2019/0216518 A1 Jul. 18, 2019

Related U.S. Application Data

(60) Continuation of application No. 15/046,295, filed on Feb. 17, 2016, now Pat. No. 10,213,243, which is a
(Continued)

(30) Foreign Application Priority Data

Aug. 10, 2011 (FR) ...................................... 1157282

(51) Int. Cl.
*A61F 2/46* (2006.01)
*A61B 17/16* (2006.01)
(Continued)

(52) U.S. Cl.
CPC ............ *A61F 2/4603* (2013.01); *A61B 17/16* (2013.01); *A61B 17/1637* (2013.01);
(Continued)

(58) Field of Classification Search
CPC ....... A61B 17/92; A61B 17/921; A61B 17/16; A61B 17/1604; A61B 17/1659;
(Continued)

(56) References Cited

U.S. PATENT DOCUMENTS

| 448,126 A | 3/1891 | Craig |
|---|---|---|
| 1,065,456 A | 6/1913 | Lowrey |

(Continued)

FOREIGN PATENT DOCUMENTS

| DE | 4220217 | 12/1993 |
|---|---|---|
| DE | 10233204 | 1/2004 |

(Continued)

OTHER PUBLICATIONS

Barth, et al., "Is global humeral head offset related to intramedullary canal width? A computer tomography morphometric study," Journal of Experimental Orthopaedics, 2018, vol. 5, pp. 1-8.
(Continued)

*Primary Examiner* — Amy R Sipp
(74) *Attorney, Agent, or Firm* — Duane Morris LLP

(57) ABSTRACT

A surgical tool, enabling extraction of a prosthesis from a bony implantation site of that prosthesis, defines a proximo-distal axis and includes a distal end head adapted both to cut at least partially the bonding interface between the prosthesis and the bony material of the implantation site and to fix itself to the prosthesis by rotation centered on the proximo-distal axis, according to embodiments of the present invention.

30 Claims, 4 Drawing Sheets

Related U.S. Application Data division of application No. 13/553,610, filed on Jul. 19, 2012, now Pat. No. 9,289,218.

(60) Provisional application No. 61/509,506, filed on Jul. 19, 2011.

(51) Int. Cl.
*A61B 17/88* (2006.01)
*A61F 2/30* (2006.01)

(52) U.S. Cl.
CPC ........ *A61B 17/8872* (2013.01); *A61F 2/4607* (2013.01); *A61F 2/4612* (2013.01); *A61F 2002/30426* (2013.01); *A61F 2002/4619* (2013.01)

(58) Field of Classification Search
CPC ............ A61B 17/1664; A61B 17/1666; A61B 17/1671; A61B 17/1684; A61F 2/4603; A61F 2/4609; A61F 2/4612; A61F 2002/4619; A61F 2002/462; A61F 2002/4641
See application file for complete search history.

(56) References Cited

U.S. PATENT DOCUMENTS

| | | |
|---|---|---|
| 1,123,730 A | 1/1915 | Greenfield |
| 2,444,099 A | 6/1948 | Hennessey, Jr. |
| 2,886,081 A | 5/1959 | Cowley |
| 3,523,395 A | 8/1970 | Rutter et al. |
| 3,609,056 A | 9/1971 | Hougen |
| 3,738,217 A | 6/1973 | Walker |
| 4,042,980 A | 8/1977 | Swanson et al. |
| 4,147,464 A | 4/1979 | Watson et al. |
| 4,250,600 A | 2/1981 | Gunther |
| 4,261,062 A | 4/1981 | Amstutz et al. |
| 4,406,023 A | 9/1983 | Harris |
| 4,550,450 A | 11/1985 | Kinnett |
| 4,623,353 A | 11/1986 | Buechel et al. |
| 4,632,111 A | 12/1986 | Roche |
| 4,743,262 A | 5/1988 | Tronzo |
| 4,865,605 A | 9/1989 | Dines et al. |
| 4,883,491 A | 11/1989 | Mallory et al. |
| 4,919,670 A | 4/1990 | Dale et al. |
| 4,964,865 A | 10/1990 | Burkhead et al. |
| 4,986,833 A | 1/1991 | Worland |
| 5,026,373 A | 6/1991 | Ray et al. |
| 5,032,132 A | 7/1991 | Matsen et al. |
| 5,044,393 A | 9/1991 | Jiles |
| 5,080,673 A | 1/1992 | Burkhead et al. |
| 5,112,338 A | 5/1992 | Anspach, III |
| 5,163,964 A | 11/1992 | Lazzeri et al. |
| 5,171,277 A | 12/1992 | Roger |
| 5,257,995 A | 11/1993 | Umber et al. |
| 5,282,865 A | 2/1994 | Dong |
| 5,358,526 A | 10/1994 | Tornier |
| 5,489,309 A | 2/1996 | Lackey et al. |
| 5,489,310 A | 2/1996 | Mikhail |
| 5,507,817 A | 4/1996 | Craig et al. |
| 5,540,697 A | 7/1996 | Rehmann et al. |
| 5,658,290 A | 8/1997 | Lechot |
| 5,681,134 A | 10/1997 | Ebert |
| 5,702,486 A | 12/1997 | Craig et al. |
| 5,723,018 A | 3/1998 | Cyprien et al. |
| 5,776,194 A | 7/1998 | Mikol et al. |
| 5,800,551 A | 9/1998 | Williamson et al. |
| 5,810,524 A | 9/1998 | Wirth, Jr. et al. |
| 5,820,315 A | 10/1998 | Collard |
| 5,830,215 A | 11/1998 | Incavo et al. |
| 5,904,688 A | 5/1999 | Gilbert et al. |
| 5,954,727 A | 9/1999 | Collazo |
| 5,976,148 A | 11/1999 | Charpenet et al. |
| 6,045,582 A | 4/2000 | Prybyla |
| 6,063,124 A * | 5/2000 | Amstutz .................. A61F 2/34 623/22.21 |
| 6,099,214 A | 8/2000 | Lee et al. |
| 6,132,469 A | 10/2000 | Schroeder |
| 6,139,551 A | 10/2000 | Michelson et al. |
| 6,146,423 A | 11/2000 | Cohen et al. |
| 6,174,335 B1 | 1/2001 | Varieur et al. |
| 6,187,012 B1 | 2/2001 | Masini |
| 6,197,063 B1 | 3/2001 | Dews |
| 6,264,299 B1 | 7/2001 | Noda |
| 6,264,657 B1 | 7/2001 | Urbahns et al. |
| 6,306,171 B1 | 10/2001 | Conzemius |
| 6,364,910 B1 | 4/2002 | Shultz et al. |
| 6,368,271 B1 | 4/2002 | Sharratt |
| 6,368,353 B1 | 4/2002 | Arcand |
| 6,379,917 B1 | 4/2002 | Oku et al. |
| 6,409,730 B1 | 6/2002 | Green et al. |
| 6,508,840 B1 | 1/2003 | Rockwood, Jr. et al. |
| 6,520,994 B2 | 2/2003 | Nogarin |
| 6,537,278 B1 | 3/2003 | Johnson |
| 6,666,874 B2 | 12/2003 | Heitzmann et al. |
| 6,736,851 B2 | 5/2004 | Maroney et al. |
| 6,746,452 B2 | 6/2004 | Tuke et al. |
| 6,783,549 B1 | 8/2004 | Stone et al. |
| 6,786,684 B1 | 9/2004 | Ecker |
| 6,797,006 B2 | 9/2004 | Hodorek et al. |
| 7,044,973 B2 | 5/2006 | Rockwood, Jr. et al. |
| 7,097,663 B1 | 8/2006 | Nicol et al. |
| 7,140,087 B1 | 11/2006 | Giltner |
| 7,160,328 B2 | 1/2007 | Rockwood, Jr. et al. |
| 7,169,184 B2 | 1/2007 | Dalla Pria |
| 7,175,663 B1 | 2/2007 | Stone |
| 7,179,084 B1 | 2/2007 | Kometas |
| 7,189,036 B1 | 3/2007 | Watson |
| 7,189,261 B2 | 3/2007 | Dews et al. |
| 7,204,854 B2 | 4/2007 | Guederian et al. |
| 7,344,565 B2 | 3/2008 | Seyer et al. |
| 7,465,319 B2 | 12/2008 | Tornier |
| 7,476,228 B2 | 1/2009 | Abou |
| 7,476,253 B1 | 1/2009 | Craig et al. |
| 7,585,327 B2 | 9/2009 | Winslow |
| 7,615,080 B2 | 11/2009 | Ondrla |
| 7,637,703 B2 | 12/2009 | Khangar et al. |
| 7,648,530 B2 | 1/2010 | Habermeyer et al. |
| 7,670,382 B2 | 3/2010 | Parrott et al. |
| 7,678,150 B2 | 3/2010 | Tornier et al. |
| 7,744,602 B2 | 6/2010 | Teeny et al. |
| 7,758,650 B2 | 7/2010 | Dews et al. |
| 7,887,544 B2 | 2/2011 | Tornier et al. |
| 7,927,376 B2 | 4/2011 | Leisinger et al. |
| D643,926 S | 8/2011 | Collins |
| 8,021,370 B2 | 9/2011 | Fenton et al. |
| 8,114,089 B2 | 2/2012 | Divoux et al. |
| 8,162,947 B2 | 4/2012 | Dreyfuss |
| 8,182,541 B2 | 5/2012 | Long et al. |
| 8,187,282 B2 | 5/2012 | Tornier et al. |
| 8,192,497 B2 | 6/2012 | Ondrla |
| 8,202,275 B2 | 6/2012 | Wozencroft |
| 8,221,037 B2 | 7/2012 | Neitzell |
| 8,231,682 B2 | 7/2012 | LaFosse |
| 8,246,687 B2 | 8/2012 | Katrana et al. |
| 8,277,512 B2 | 10/2012 | Parrott et al. |
| 8,317,871 B2 | 11/2012 | Stone et al. |
| 8,409,798 B2 | 4/2013 | Luy et al. |
| 8,419,798 B2 | 4/2013 | Ondrla et al. |
| D685,474 S | 7/2013 | Courtney |
| 8,500,744 B2 | 8/2013 | Wozencroft et al. |
| 8,506,638 B2 | 8/2013 | Vanasse et al. |
| 8,512,410 B2 | 8/2013 | Metcalfe et al. |
| 8,545,506 B2 | 10/2013 | Long et al. |
| 8,591,592 B2 | 11/2013 | Dreyfuss |
| 8,641,773 B2 | 2/2014 | Bergin et al. |
| 8,690,958 B2 | 4/2014 | Klawitter et al. |
| 8,702,800 B2 | 4/2014 | Linares et al. |
| 8,753,402 B2 | 6/2014 | Winslow et al. |
| 8,840,671 B2 | 9/2014 | Ambacher |
| 8,845,742 B2 | 9/2014 | Kusogullari et al. |
| 8,864,834 B2 | 10/2014 | Boileau et al. |
| 8,870,962 B2 | 10/2014 | Roche et al. |

(56) References Cited

U.S. PATENT DOCUMENTS

| | | |
|---|---|---|
| 8,876,908 B2 | 11/2014 | Katrana et al. |
| 8,882,845 B2 | 11/2014 | Wirth et al. |
| D745,678 S | 12/2015 | Courtney et al. |
| 9,233,003 B2 | 1/2016 | Roche et al. |
| 9,289,218 B2 | 3/2016 | Courtney, Jr. et al. |
| 9,326,865 B2 | 5/2016 | Katrana et al. |
| 9,498,345 B2 | 11/2016 | Brukhead, Jr. et al. |
| D840,539 S | 2/2019 | Courtney et al. |
| 10,456,264 B2 | 10/2019 | Hodorek et al. |
| 10,463,499 B2 | 11/2019 | Emerick et al. |
| 2001/0034553 A1 | 10/2001 | Michelson |
| 2001/0047210 A1 | 11/2001 | Wolf |
| 2002/0116007 A1 | 8/2002 | Lewis |
| 2002/0156534 A1 | 10/2002 | Grusin et al. |
| 2003/0004573 A1 | 1/2003 | Bagby |
| 2003/0028253 A1 | 2/2003 | Stone et al. |
| 2003/0031521 A1 | 2/2003 | Haughton et al. |
| 2003/0114933 A1 | 6/2003 | Bouttens et al. |
| 2003/0125810 A1 | 7/2003 | Sullivan et al. |
| 2004/0049270 A1 | 3/2004 | Gewirtz |
| 2004/0186586 A1 | 9/2004 | Seyer et al. |
| 2004/0193276 A1 | 9/2004 | Maroney et al. |
| 2004/0193277 A1 | 9/2004 | Long et al. |
| 2004/0193278 A1 | 9/2004 | Maroney et al. |
| 2004/0220674 A1 | 11/2004 | Pria |
| 2004/0243136 A1 | 12/2004 | Gupta et al. |
| 2005/0107882 A1 | 5/2005 | Stone et al. |
| 2005/0112397 A1 | 5/2005 | Rolfe et al. |
| 2005/0209597 A1 | 9/2005 | Long et al. |
| 2005/0261775 A1 | 11/2005 | Baum et al. |
| 2005/0267478 A1 | 12/2005 | Corradi et al. |
| 2006/0004378 A1 | 1/2006 | Raines |
| 2006/0009852 A1 | 1/2006 | Winslow et al. |
| 2006/0089656 A1 | 4/2006 | Allard et al. |
| 2006/0195105 A1 | 8/2006 | Teeny et al. |
| 2006/0200165 A1 | 9/2006 | Tulkis |
| 2006/0200249 A1 | 9/2006 | Beguin et al. |
| 2007/0010825 A1 | 1/2007 | Leisinger et al. |
| 2007/0100458 A1 | 5/2007 | Dalla Pria |
| 2007/0123890 A1 | 5/2007 | Way et al. |
| 2007/0123893 A1 | 5/2007 | O'Donoghue |
| 2007/0123909 A1 | 5/2007 | Rupp et al. |
| 2007/0156246 A1 | 7/2007 | Meswania et al. |
| 2007/0162141 A1 | 7/2007 | Dews et al. |
| 2007/0173945 A1 | 7/2007 | Wiley et al. |
| 2007/0212179 A1 | 9/2007 | Khangar et al. |
| 2007/0219562 A1 | 9/2007 | Slone et al. |
| 2007/0225817 A1 | 9/2007 | Reubelt et al. |
| 2007/0233132 A1 | 10/2007 | Valla |
| 2008/0021564 A1 | 1/2008 | Gunther |
| 2008/0077146 A1 | 3/2008 | Pernsteiner et al. |
| 2008/0195111 A1 | 8/2008 | Anderson |
| 2008/0249577 A1 | 10/2008 | Dreyfuss |
| 2009/0171462 A1 | 7/2009 | Poncet et al. |
| 2009/0281630 A1 | 11/2009 | Delince et al. |
| 2009/0306782 A1 | 12/2009 | Schwyzer |
| 2010/0042214 A1 | 2/2010 | Nebosky et al. |
| 2010/0087927 A1 | 4/2010 | Roche et al. |
| 2010/0114326 A1 | 5/2010 | Winslow et al. |
| 2010/0191340 A1 | 7/2010 | Dreyfuss |
| 2010/0274360 A1 | 10/2010 | Gunther |
| 2010/0278601 A1 | 11/2010 | Beynon |
| 2011/0153023 A1 | 6/2011 | Deffenbaugh et al. |
| 2011/0224673 A1* | 9/2011 | Smith .................. A61F 2/4081 606/87 |
| 2011/0276144 A1 | 11/2011 | Wirth et al. |
| 2011/0313533 A1 | 12/2011 | Gunther |
| 2012/0109321 A1 | 5/2012 | Stone et al. |
| 2012/0184964 A1* | 7/2012 | Hudak, Jr. ............ A61F 2/4609 606/91 |
| 2012/0221111 A1 | 8/2012 | Burkhead, Jr. et al. |
| 2012/0265315 A1 | 10/2012 | Kusogullari et al. |
| 2012/0277880 A1 | 11/2012 | Winslow et al. |
| 2012/0296435 A1 | 11/2012 | Ambacher |
| 2013/0123929 A1 | 5/2013 | McDaniel et al. |
| 2013/0123930 A1 | 5/2013 | Burt |
| 2013/0173006 A1 | 7/2013 | Duport |
| 2013/0178943 A1 | 7/2013 | Duport |
| 2013/0190882 A1 | 7/2013 | Humphrey |
| 2013/0211539 A1 | 8/2013 | McDaniel et al. |
| 2013/0261626 A1 | 10/2013 | Chavarria et al. |
| 2013/0261629 A1 | 10/2013 | Anthony et al. |
| 2013/0261754 A1 | 10/2013 | Anthony et al. |
| 2013/0282129 A1 | 10/2013 | Phipps |
| 2014/0012272 A1 | 1/2014 | Leisinger |
| 2014/0012380 A1 | 1/2014 | Laurence et al. |
| 2014/0058523 A1 | 2/2014 | Walch et al. |
| 2014/0107792 A1 | 4/2014 | Hopkins et al. |
| 2014/0156012 A1 | 6/2014 | Winslow |
| 2014/0236304 A1 | 8/2014 | Hodorek et al. |
| 2014/0257499 A1 | 9/2014 | Winslow et al. |
| 2014/0296988 A1 | 10/2014 | Winslow et al. |
| 2014/0358239 A1 | 12/2014 | Katrana et al. |
| 2014/0358240 A1 | 12/2014 | Katrana et al. |
| 2014/0379089 A1 | 12/2014 | Bachmaier |
| 2015/0134066 A1 | 5/2015 | Bachmaier |
| 2015/0250601 A1 | 9/2015 | Humphrey |
| 2015/0289984 A1 | 10/2015 | Budge |
| 2015/0297354 A1 | 10/2015 | Walch et al. |
| 2016/0051367 A1 | 2/2016 | Gervasi et al. |
| 2016/0157911 A1 | 6/2016 | Courtney, Jr. et al. |
| 2016/0324648 A1 | 11/2016 | Hodorek et al. |
| 2017/0105843 A1 | 4/2017 | Britton et al. |
| 2017/0273800 A1 | 9/2017 | Emerick et al. |
| 2017/0304063 A1 | 10/2017 | Hatzidakis et al. |
| 2017/0367836 A1 | 12/2017 | Cardon et al. |
| 2019/0159906 A1 | 5/2019 | Knox et al. |
| 2019/0175354 A1 | 6/2019 | Knox et al. |

FOREIGN PATENT DOCUMENTS

| | | |
|---|---|---|
| DE | 102004042502 | 3/2006 |
| EP | 0 274 094 | 8/1990 |
| EP | 1 413 265 | 4/2004 |
| EP | 0 959 822 | 5/2004 |
| EP | 1 125 565 | 12/2004 |
| EP | 1 518 519 | 3/2005 |
| EP | 1 004 283 | 5/2005 |
| EP | 1 639 967 | 3/2006 |
| EP | 1 762 191 | 3/2007 |
| EP | 1 952 788 | 8/2008 |
| EP | 1 867 303 | 9/2010 |
| EP | 1 977 720 | 1/2011 |
| EP | 1 550 420 | 2/2012 |
| EP | 2 261 303 | 11/2012 |
| EP | 1 706 074 | 12/2012 |
| EP | 2 564 814 | 3/2013 |
| EP | 2 567 676 | 3/2013 |
| EP | 2 574 313 | 4/2013 |
| EP | 2 616 013 | 7/2013 |
| EP | 2 474 288 | 9/2013 |
| EP | 2 663 263 | 5/2014 |
| EP | 2 502 605 | 8/2014 |
| EP | 2 800 541 | 11/2014 |
| EP | 2 815 726 | 8/2015 |
| EP | 2 353 549 | 6/2016 |
| EP | 3 117 801 | 1/2017 |
| EP | 2 965 720 B1 | 7/2017 |
| FR | 2 674 122 | 9/1992 |
| FR | 2997290 B1 | 11/2015 |
| WO | WO 01/67988 | 9/2001 |
| WO | WO 02/17822 | 3/2002 |
| WO | WO 2008/011078 | 1/2008 |
| WO | WO 2008/146124 | 12/2008 |
| WO | WO 2011/081797 | 7/2011 |
| WO | WO 2012/035263 | 3/2012 |
| WO | WO 2012/130524 | 10/2012 |
| WO | WO 2013/009407 | 1/2013 |
| WO | WO 2013/064569 | 5/2013 |
| WO | WO 2013/148229 | 10/2013 |
| WO | WO 2014/005644 | 1/2014 |
| WO | WO 2014/058314 | 4/2014 |
| WO | WO 2015/112307 | 7/2015 |
| WO | WO2016094739 A1 | 6/2016 |

(56) References Cited

FOREIGN PATENT DOCUMENTS

| WO | WO 2017/165090 | 9/2017 |
| WO | WO 2017/184792 | 10/2017 |
| WO | WO 2018/022227 | 2/2018 |
| WO | WO 2019/060780 | 3/2019 |

OTHER PUBLICATIONS

Boileau, et al., "The Three-Dimensional Geometry of the Proximal Humerus: Implications for Surgical Technique and Prosthetic Design," J Bone Joint Surg, Sep. 1997, vol. 79-B, Issue 5, pp. 857-865.

Routman, et al., "Reverse Shoulder Arthroplasty Prosthesis Design Classification System," Bulletin of the Hospital for Joint Diseases, 2015, vol. 73 (Suppl 1), pp. S5-S14.

French Search report issued in Application No. FR1157282, dated Feb. 27, 2012, in 1 page.

Non-Final Office Action issued in connection with U.S. Appl. No. 17/250,964, filed Jul. 26, 2021, 27 pages.

Final Rejection issued in connection with U.S. Appl. No. 16/249,720, filed Aug. 20, 2021, 40 pages.

Final Rejection issued in connection with U.S. Appl. No. 16/580,367, filed Aug. 24, 2021, 9 pages.

Non-Final Office Action issued in connection with U.S. Appl. No. 16/519,937, filed Aug. 17, 2021, 21 pages.

Final Office Action issued in connection with U.S. Appl. No. 17/250,964, filed Sep. 9, 2021, 22 pages.

\* cited by examiner

OSTEOTOME EXTRACTOR

CROSS-REFERENCE TO RELATED APPLICATION

This application is a continuation of U.S. patent application Ser. No. 15/046,295, filed on Feb. 17, 2016, which is a divisional of U.S. patent application Ser. No. 13/553,610, now U.S. Pat. No. 9,289,218, filed on Jul. 19, 2012, which claims the benefit of U.S. Provisional Patent Application Ser. No. 61/509,506, filed on Jul. 19, 2011, and claims foreign priority to French Patent Application No. 20110057282, filed Aug. 10, 2011, both of which are incorporated by reference herein in their entireties for all purposes.

TECHNICAL FIELD

Embodiments of the present invention relate to a surgical tool for extraction of a prosthesis from a bony implantation site of that prosthesis as well as a surgical kit including such a surgical tool and such a prosthesis.

BACKGROUND

When a prosthesis has been implanted in a bone for a certain time, typically several years, it may prove necessary to remove the prosthesis for various reasons: for example, wear of the prosthesis, degeneration of the bony material of the prosthesis implantation site, trauma, and the like. The prosthesis removed is generally replaced by a revision prosthesis, the success and the implantation performance of which depend on the residual stock of bony material after removing the initial prosthesis. Consequently, surgeons aim to limit as much as possible any cutting of bony material necessary to free and extract the initial prosthesis.

With the arrival of prostheses with a porous surface or, more generally, adapted to have their surface colonized by the bone of the implantation site, extraction operations may prove particularly delicate. To this end, the surgeon generally employs osteotomes, the application of which may advantageously be guided to improve the precision of their action. Then, once the bonding interface between the prosthesis and the bony material has been cut in this way by these osteotomes, the surgeon uses another surgical tool to grasp and pull on the prosthesis in order to extract it.

SUMMARY

Embodiments of the present invention include an improved extraction surgical tool that facilitates and enhances the gestures of the surgeon. Embodiments of the present invention include a surgical tool for extraction of a prosthesis from a bony implantation site of that prosthesis, the surgical tool defining a proximo-distal axis and including a distal end head adapted both to cut at least partially the bonding interface between the prosthesis and the bony material of the implantation site and to fix itself to the prosthesis by a bayonet connection centered on the proximo-distal axis.

Embodiments of the present invention may also include a surgical kit, including a surgical tool as described above and a bone implantation prosthesis that includes a body to be anchored in the bony material of the implantation site, the anchor carrying externally at least part of the bonding interface between the prosthesis and the bony material of the implantation site and including a flange bearing on the implantation site, this flange being adapted to be fixed to the distal end head of the surgical tool by the bayonet connection.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
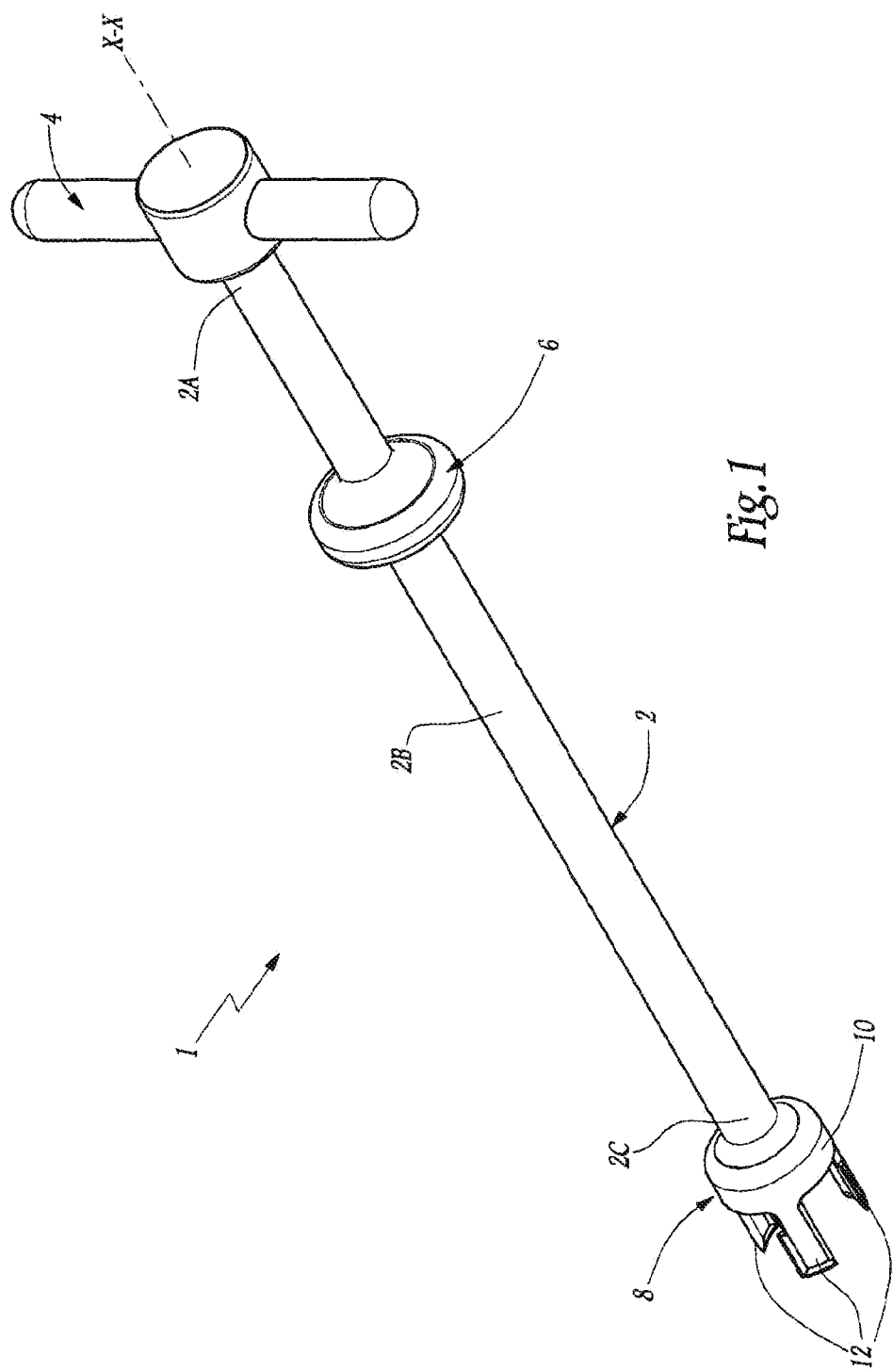
FIG. 1 is a perspective view of a surgical tool, according to embodiments of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 2:
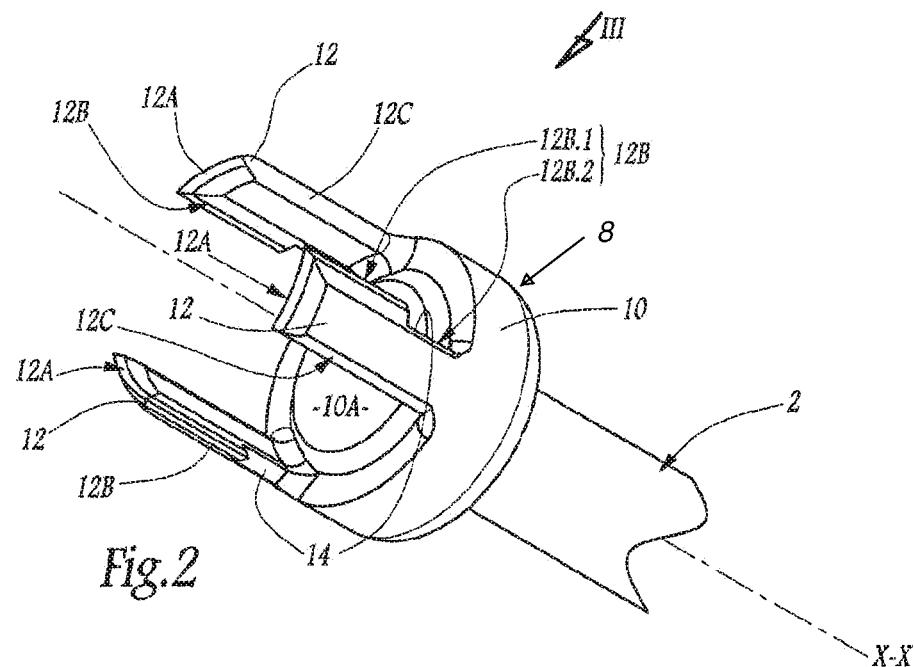
FIG. 2 is a perspective view as seen from a different angle and to a larger scale than FIG. 1 of a portion of the surgical tool from FIG. 1, according to embodiments of the present invention.
Figure 3:
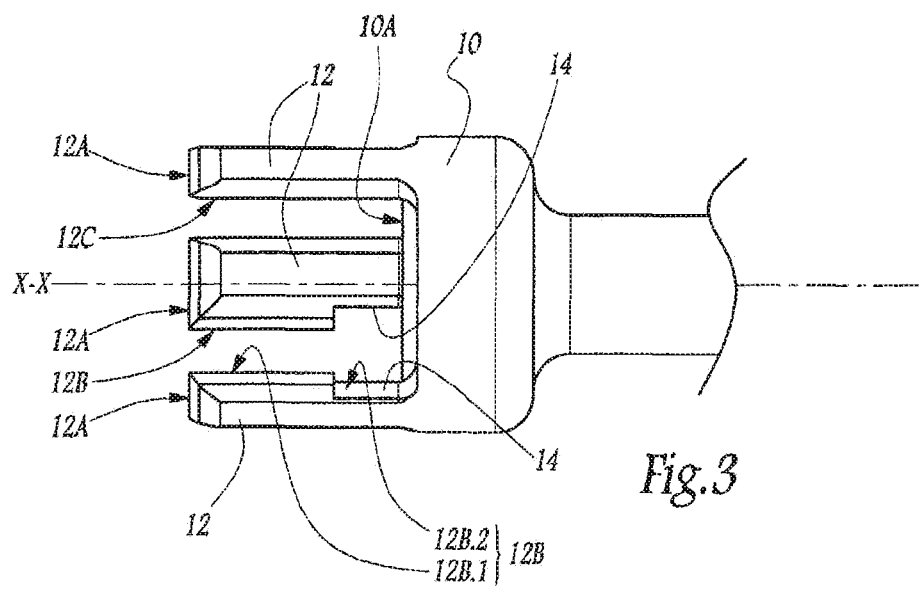
FIG. 3 is a view in elevation in the direction of the arrow III in FIG. 2, according to embodiments of the present invention.

In FIGS. 1 to 3 there is represented a surgical tool 1 for extracting a prosthesis from a bony implantation site of that prosthesis. As seen clearly in FIG. 1, this surgical tool 1 has an elongate overall shape, centered on a longitudinal axis X-X which, in use, extends in a direction which, at the proximal end, faces toward the surgeon and, at the distal end faces toward the bony implantation site of the prosthesis to be extracted.

The surgical tool 1 includes a shaft 2 that is centered on and extends lengthwise along the axis X-X and which includes a cylindrical rod of circular section. At its proximal end 2A, the shaft 2 is provided with a fixed handle 4 arranged transversely to the axis X-X, in order to facilitate driving, for example manual driving, of the surgical tool 1 by a user. This handle 4 may be formed in the shape of a "T". In its main part 2B, the shaft 2 is fixedly provided with a shoulder 6 projecting radially from the rest of the shaft 2. The shoulder 6 may be comprised of a disc centered on the axis X-X. Alternatively, shoulder 6 may be a cylindrical handle, a roughened surface, one or more indentations, one or more protrusions, or any other shape which permits shoulder 6 to receive a traction force and transmit the traction force to the shaft, according to embodiments of the present invention.

At its end 2C, the shaft 2 includes a fixed head 8 that cooperates mechanically with a prosthesis to be extracted. As illustrated in FIGS. 1 to 3, this head 8 includes a main body 10 that is centered on the axis X-X and is generally disc-shaped. According to one embodiment, the head 8 includes three elements 12, which may be separate and identical. In other embodiments, the head 8 may include one, two, three, four, five, six or more elements 12. In still other embodiments, the elements 12 may not be identical and one or more element 12 may have different lengths, widths, thicknesses, curvatures, or other features as compared to one or more other elements 12. Each element 12 may have a shape that is elongate in the direction of the axis X-X and projects in the longitudinal axial direction from the distal face 10A of the main body 10 of the head 8. According to some embodiments of the present invention, each element 12 projects from a portion of the external periphery of the distal face 10A of the body 10. Each element 12 as a whole corresponds to a portion of a tubular wall centered on the axis X-X and projecting axially from the exterior periphery of the face 10A of the body 10, according to embodiments of the present invention. Elements 12 may be referred to as cutting elements, according to embodiments of the present invention.

According to one embodiment, the three elements 12 are distributed, for example, in a substantially regular manner (e.g. separated by substantially the same radial angles) around the axis X-X. In particular, these three elements 12 may correspond to respective portions of the same tubular wall. According to other embodiments, the two or more elements 2 are distributed in an irregular manner on the distal head 8, and are either not separated by similar radial angles, and/or are not situated about a perimeter of the distal head 8. For example, the elements 12 may be positioned on distal head 8 at different or staggered radial distances from the axis X-X, and may be positioned at different or staggered radial separations with respect to the axis X-X.

As shown in FIGS. 1 to 3, each element 12 has, axially opposite its proximal end connecting the rest of the element to the main body 10 of the head 8, a distal free edge 12A along which a cutting edge is formed in a direction peripheral to the axis X-X. Each element 12 may be delimited in a direction peripheral to the axis X-X by two opposite longitudinal free edges 12B and 12C. The longitudinal edge 12B, which is that oriented in the clockwise direction about the axis X-X when the head 8 is viewed from the proximal end 2A of the shaft 2, has, in its longitudinal direction, a distal end part 126.1 along which a cutting edge is formed and a proximal end part 126.2 in which a recessed notch 14 is delimited. Edge 12B may also be referred to as leading edge 12B, and edge 12C may be referred to as trailing edge 12C, according to embodiments of the present invention.

An example of use of the surgical tool 1 will now be described with reference to FIGS. 4 to 6.

Figure 4:
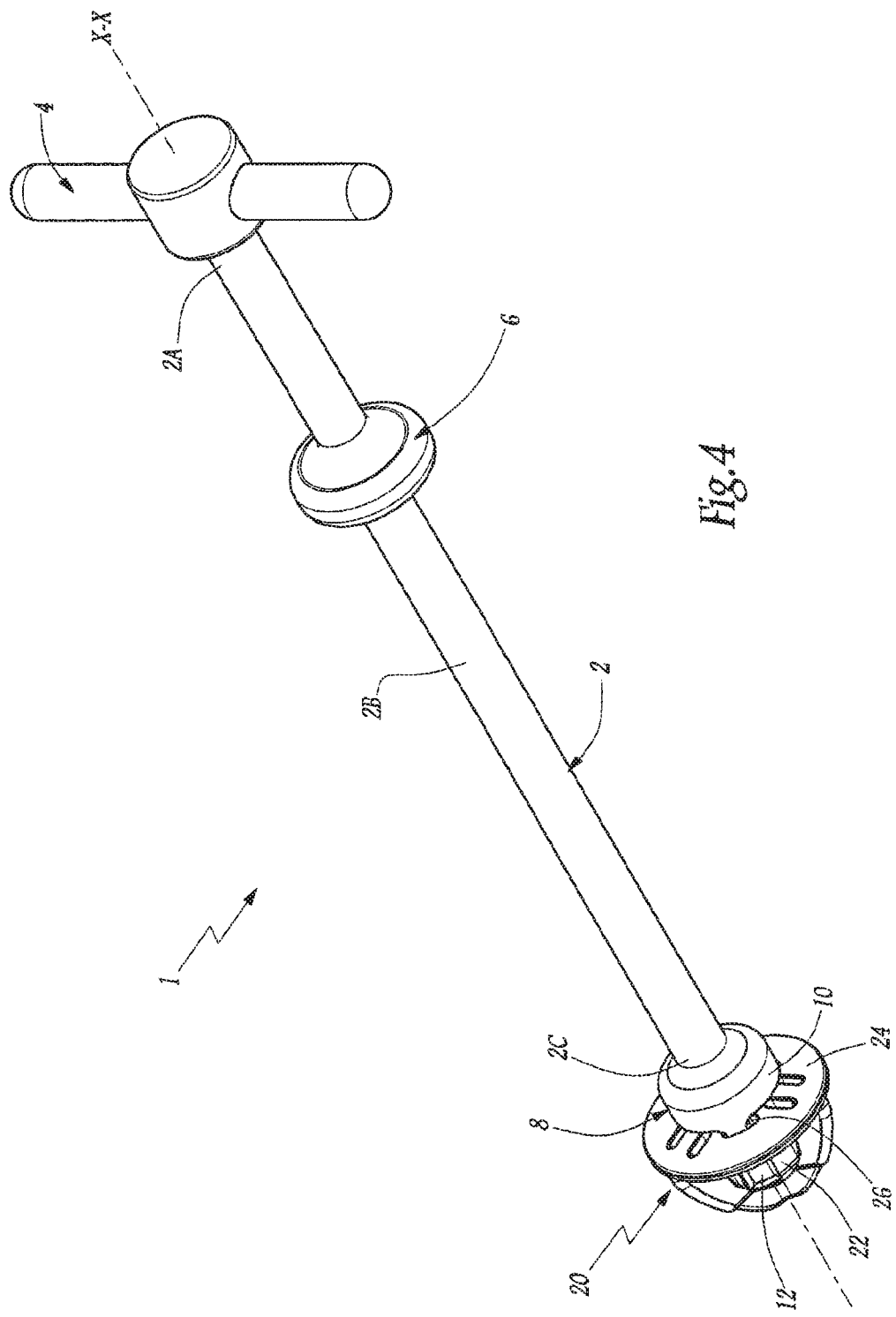
FIGS. 4 to 6 are views similar to FIGS. 1 to 3, respectively, showing the surgical tool from FIG. 1 associated with a prosthesis to be extracted with the aid of that surgical tool.
Figure 5:
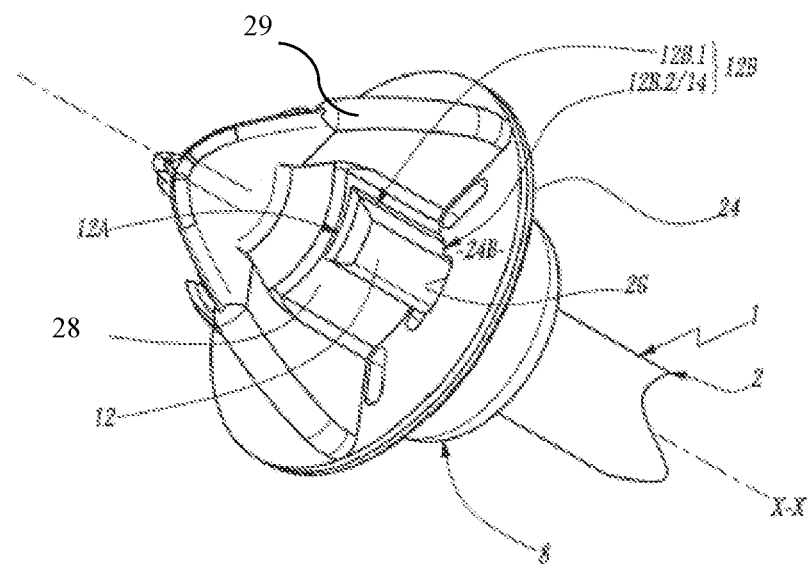
Figure 6:
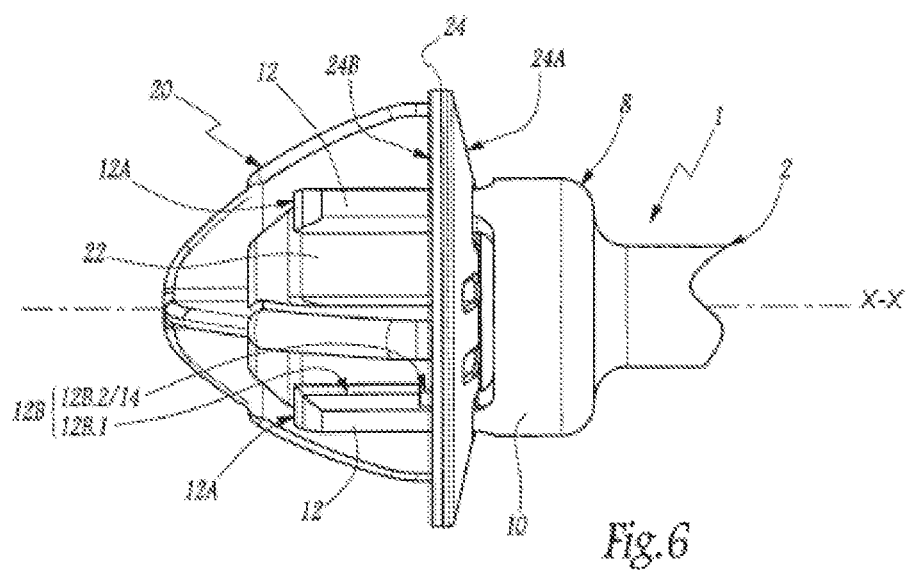

In these FIGS. 4 to 6, the head 8 of the surgical tool 1 cooperates with a prosthesis 20 to be extracted including an anchor body 22 anchored in the bony material of an implantation site of the prosthesis. This anchor body 22 is provided with a flange 24 which bears on the aforementioned implantation site. That is, the prosthesis 20 includes an anchor body 22 extending from the flange 24 along a longitudinal axis of the prosthesis 20 where the anchor body 22 includes a cylindrical body 28 and a plurality of arms 29 extending from the cylindrical body 28. In some embodiments of the present invention, when the prosthesis 20 is in an implantation configuration, its body 22 is engaged depthwise in the bony material of the implantation site and its flange 24 remains outside or partially outside the bony material of the implantation site, bearing on the perimeter surface of the hole at the implantation site in which the body 22 is housed. Consequently, if a surgeon wishes to extract the prosthesis 20 from the aforementioned implantation site, the proximal face 24A of the flange 24 is directly accessible, whereas the distal face 24B of the flange 24 bears on the bony material of the implantation site. Given the context of the surgical intervention, the interface between the prosthesis 20, and more precisely the body 22 of that prosthesis, and the bony material of the implantation site proves resistant to extraction of the prosthesis 20 in the sense that, over time, a mechanical-biological bond has progressively formed at this interface between the prosthesis and the bony material. The strength of this bonding interface often proves particularly high in the situation in which the body 22 has a porous structure or, more generally, an exterior surface suitable for osteo-integration, as is generally the case when the prosthesis 20 is a prosthesis implanted without cement.

As used herein, the term "flange" is used in its broadest sense to refer to any structure or shape which has a proximal surface and a distal surface and is capable of contacting bone or being positioned on or near bone. For example, a flange may have a circular, square, rectangular, triangular, or other (regular or irregular) polygonal shaped cross-section along a dimension that is substantially perpendicular to the axis X-X, according to embodiments of the present invention. The perimeter of the flange may be smooth and/or continuously contoured, or may include straight segments, and/or may include a combination of both contoured and straight segments.

To extract the prosthesis 20, the surgeon grasps the shaft 2 of the surgical tool 1, notably by hand, and moves the head 8 toward the prosthesis 20, substantially aligning the axis X-X with a central geometrical axis of the prosthesis 20, in particular the central geometrical axis around which the flange 24 extends peripherally. The distal edge 12A of each element 12 of the head 8 can then be used to cut at least in part the bonding interface between the prosthesis 20 and the bony material of the implantation site. To this end, the flange 24 is provided with three through-slots 26 each of which connects the proximal face 24A and the distal face 24B of the flange 24 to each other. Each slot 26 has a cross section allowing, or even in some cases guiding, introduction into this slot of one of the elements 12, in a movement in translation oriented along the axis X-X and directed in the distal direction. In other words, each slot 26 may have a cross-sectional shape corresponding to a flat ring portion the width of which considered radially with respect to the axis X-X substantially corresponds to the radial thickness of each element 12 and the length of which, in a direction peripheral to the axis X-X, is substantially equal to the peripheral extent of the element 12, as illustrated in FIGS. 4 and 5, according to embodiments of the present invention.

The distal edge 12A of the elements 12 is introduced first into one of the slots 26 and projects therefrom, at the distal end, cutting the portion of the (bony) bonding interface between the prosthesis 20 and the bony material that it encounters on its trajectory in translation. The surgeon continues to drive the surgical tool 1 in translation distally along the axis X-X until the distal face 10A of the body 10 comes to bear against or in the immediate vicinity of the proximal face of the prosthesis 20, for example with the interior periphery of the proximal face 24A of the flange 24.

The surgeon then rotates the shaft 2 on itself about the axis X-X, in some cases using the handle 4 to increase the driving torque. In some cases, use of the handle 4 increases the driving torque tenfold. The head 8 is then driven in a similar rotary movement, causing the longitudinal edge 12B of each of its elements 12 to follow a circular trajectory, centered on the axis X-X, and, in the embodiment shown, in the clockwise direction. The distal end part 12B.1 of each of the edges 12B then cuts the part of the bonding interface between the body 22 of the prosthesis 20 and the bony material of the implantation site, situated on the circular trajectory of the edge 12B. At the same time, each notch 14 of the longitudinal edges 12 mechanically engages the flange 24 in the direction in which, given the rotary movement of the head 8 on itself about the axis X-X relative to the prosthesis 20, one of the peripheral ends of each slot 26 is introduced into the notch 14. This cases the slots 26 to become engaged, in a direction peripheral to the axis X-X, axially between the opposite axial edges of the notch 14. This rotation drive movement is continued by the surgeon so as to engage the flange 24 as far as to the bottom of the notches 14. The surgical tool 1 and the prosthesis 20 are then in the configuration of use represented in FIGS. 4 to 6.

Although notch 14 is shown as having an "L" shape, notch 14 may alternatively have other shapes, according to embodiments of the present invention. For example, the shape of notch 14 may be fully or partially curved, for example in a "U" shape, or may be segmented, for example in a "V" shape, according to embodiments of the present invention. Notch 14 may include any shape which is capable of accepting at least a portion of the inside edge of an aperture 26 upon rotation of the head 8, according to embodiments of the present invention. In one embodiment, the proximal end of notch 14 is delimited by a distal surface of the head 8 as shown in FIG. 3. In another embodiment, the proximal edge of notch 14 is located distally of the distal surface of the head 8. The shape of the proximal edge of the notch 14 may also take numerous forms, for example straight, curved, or a combination of straight and curved, according to embodiments of the present invention.

Although clockwise rotation is described, one of ordinary skill will appreciate, based on the present disclosure, that the tool 1 may alternatively be configured for counterclockwise rotation, according to embodiments of the present invention.

Upon engagement of the tool 1 with the prosthesis 20, the mechanical connection that the surgeon establishes between the head 8 of the surgical tool 1 and the flange 24 of the prosthesis 20 is a bayonet connection centered on the axis X-X, according to embodiments of the present invention.

The surgeon may exert a traction force along the axis X-X, directed in the proximal direction. The surgeon makes use of the shoulder 6, for example by mechanically engaging this shoulder 6 with an ad hoc tool (not shown), enabling the surgeon to increase (e.g. tenfold) the applied force to apply to the shaft 2 axial traction loads directed in the proximal direction. As the bonding interface between the prosthesis 20 and the bony material of the prosthesis implantation site has been cut in several areas, by the successive action of the distal edges 12A and the distal end parts 12B.1 of the longitudinal edges 12B of the elements 12, remaining uncut areas of this bonding interface are broken in a controlled manner as to their location, and easily, without the surgeon having to exert too great a traction force.

Thus the surgical tool 1 enables the prosthesis 20 to be extracted easily and quickly, it being noted that, due at least in part to its bayonet fixing, integrating partial cutting of the bonding interface between the prosthesis and the bony material of the implantation site, the surgeon does not need to use two separate instruments to turn and turn about to cut the aforementioned interface and then make the mechanical attachment to the prosthesis to be pulled.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A system comprising:
   an implant including a plurality of apertures; and
   a tool including a plurality of elongate elements extending distally from a main body of the tool along a direction that is substantially parallel to a longitudinal axis of the tool, each of the plurality of elongate elements including:
   a first edge extending in a longitudinal direction;
   a second edge opposite the first edge and extending in the longitudinal direction; and
   a distal edge extending between the first edge and the second edge; wherein
   each of the plurality of elongate elements is configured to extend through a corresponding one of the plurality of apertures of the implant and along an exterior surface of a cylindrical body of the implant; and
   the first edge and the distal edge of each of the plurality of elongate elements are configured to physically contact with and partially separate an interface between the cylindrical body of the implant and bony material at the exterior surface of the cylindrical body of the implant.

2. The system of claim 1, wherein the first edge is a cutting edge.

3. The system of claim 1, wherein the first edge and the second edge of each of the plurality of elongate elements is entirely radially inward of an outer face of the respective elongate element.

4. The system of claim 1, wherein a first portion of the first edge is a cutting edge and a second portion of the first edge is configured to engage with a flange of the implant.

5. The system of claim 1, wherein each of the plurality of elongate elements extends along a portion of a tubular periphery centered on the longitudinal axis.

6. The system of claim 1, wherein the plurality of elongate elements are spaced apart by substantially a same circumferential separation.

7. The system of claim 1, wherein the plurality of elongate elements comprises at least three elongate elements.

8. The system of claim 1, wherein, in use, a distal end of each of the elongate elements is at a distal-most edge of the tool.

9. The system of claim 1, wherein
   the tool further includes a shaft extending along the longitudinal axis,
   a distal end of the shaft is affixed to the main body, and
   a driving handle is affixed to a proximal end of the shaft.

10. The system of claim 1, wherein each of the plurality of elongate elements is configured to couple with the corresponding one of the plurality of apertures upon rotation of the tool about the longitudinal axis.

11. The system of claim 1, wherein the implant comprises a flange, the flange comprising a proximal surface and a distal surface, wherein the distal surface is configured to bear on the implantation site, wherein the flange comprises the plurality of apertures.

12. The system of claim 1, wherein the tool is configured to extract the implant.

13. A system comprising:
    an implant including a flange having a proximal surface and a distal surface, the flange including a plurality of slots extending between the proximal surface and the distal surface, the plurality of slots being circumferentially spaced apart from each other; and a tool including a plurality of elongate elements extending distally from a main body of the tool along a direction that is substantially parallel to a longitudinal axis of the tool;

wherein each of the plurality of elongate elements is configured to extend through a corresponding one of the plurality of the slots of the implant and along an exterior surface of a cylindrical body of the implant, the cylindrical body being enclosed, and include a cutting edge to physically contact and separate an interface between the implant and bony material at an implantation site of the implant.

14. The system of claim 13, wherein the implant comprises an anchor body extending from the flange along a longitudinal axis of the implant, the anchor body including the cylindrical body and a plurality of longitudinal structures extending from the cylindrical body.

15. The system of claim 14, wherein each of the plurality of slots has a first edge arranged with a radially outer periphery of the cylindrical body and a second edge spaced radially outward from the first edge, the first edge and the second edge separated by a gap.

16. The system of claim 14, wherein each of the plurality of slots is configured to guide a corresponding one of the plurality of elongate elements between two of the plurality of longitudinal structures of the implant.

17. The system of claim 13, wherein each of the plurality of slots is shaped to guide introduction of a corresponding one of the plurality of elongate elements.

18. The system of claim 13, wherein each of the plurality of slots is configured to guide longitudinal translation of a corresponding one of the plurality of elongate elements.

19. The system of claim 13, wherein a width, measured radially with respect to a longitudinal axis of the implant, of each of the plurality of slots corresponds to a radial thickness of a corresponding one of the plurality of elongate elements.

20. The system of claim 13, wherein a length, measured in a direction transverse to a longitudinal axis of the implant, of each of the plurality of slots is substantially equal to a peripheral extent of a corresponding one of the plurality of elongate elements.

21. The system of claim 13, wherein the implant comprises a cylindrical anchor body extending from the flange and each of the elongate elements has a curvature corresponding to the curvature of the cylindrical anchor body.

22. The system of claim 13, wherein the tool is configured to extract the implant.

23. A system comprising:
an implant including a plurality of apertures; and
a tool including:
    a main body; and
    a separator including an edge to physically contact and separate an interface between an exterior surface of an enclosed cylindrical body of the implant and bony material at the exterior surface of the enclosed cylindrical body of the implant, the separator interfacing with the plurality of apertures in the implant.

24. The system of claim 23, wherein the implant comprises a flange having a proximal surface and a distal surface, the flange comprising the plurality of apertures.

25. The system of claim 23, wherein the plurality of apertures are circumferentially spaced apart from each other.

26. The system of claim 23, wherein the implant incudes an anchor body extending from a flange along a longitudinal axis of the implant, the anchor body including the enclosed cylindrical body and a plurality of longitudinal structures extending from the cylindrical body.

27. The system of claim 23, wherein the plurality of apertures are configured to guide longitudinal translation of the tool.

28. The system of claim 23, wherein the separator includes a notch defined along a direction extending distally of the main body.

29. The system of claim 23, wherein a notch is defined along a circumferential edge of the separator.

30. The system of claim 23, wherein the tool is configured to extract the implant.

\* \* \* \* \*

UNITED STATES PATENT AND TRADEMARK OFFICE
CERTIFICATE OF CORRECTION

PATENT NO. : 11,278,428 B2
APPLICATION NO. : 16/249720
DATED : March 22, 2022
INVENTOR(S) : Robert Courtney and Jeffrey M. Ondrla It is certified that error appears in the above-identified patent and that said Letters Patent is hereby corrected as shown below:

In the Claims

Column 6 Claim 1, Line 2, "an implant including a plurality of apertures; and" should read -- an implant including a cylindrical body and a plurality of apertures; and --;

Column 6 Claim 1, Lines 15-16, "apertures of the implant and along an exterior surface of a cylindrical body of the implant; and" should read -- apertures of the implant and along a cylindrical exterior surface of the cylindrical body of the implant; and --;

Column 6 Claim 1, Lines 20-21, "cylindrical body of the implant and bony material at the exterior surface of the cylindrical body of the implant." should read -- cylindrical body of the implant and bony material at the cylindrical exterior surface of the cylindrical body of the implant. --;

Column 6 Claim 13, Line 2, "an implant including a flange having a proximal surface" should read -- an implant including a cylindrical body and a flange having a proximal surface --;

Column 7 Claim 13, Lines 13-14, "the plurality of the slots of the implant and along an exterior surface of a cylindrical body of the implant, the" should read -- the plurality of the slots of the implant and along a cylindrical exterior surface of the cylindrical body of the implant, the --;

Column 8 Claim 23, Line 2, "an implant including a plurality of apertures; and" should read -- an implant including an enclosed cylindrical body and a plurality of apertures; and --;

Signed and Sealed this
Twenty-fourth Day of May, 2022

*Katherine Kelly Vidal*

Katherine Kelly Vidal
*Director of the United States Patent and Trademark Office*

Column 8 Claim 23, Lines 6-9, "separate an interface between an exterior surface of an enclosed cylindrical body of the implant and bony material at the exterior surface of the enclosed cylindrical body of the implant, the separator interfacing" should read -- separate an interface between a cylindrical exterior surface of the enclosed cylindrical body of the implant and bony material at the cylindrical exterior surface of the enclosed cylindrical body of the implant, the separator interfacing --.